US006455303B1

(12) United States Patent
Orwar et al.

(10) Patent No.: US 6,455,303 B1
(45) Date of Patent: Sep. 24, 2002

(54) DETECTION OF BIOLOGICALLY ACTIVE MOLECULES BY USE OF PRE-ACTIVATED CELL-BASED BIOSENSORS IN LIQUID-BASED SEPARATION SYSTEMS

(75) Inventors: Owe Orwar, Hovås; Kent Jardemark, Tyresö, both of (SE)

(73) Assignee: Cellectricon AB, Goteborg (SE)

( * ) Notice: Subject to any disclaimer, the term of this patent is extended or adjusted under 35 U.S.C. 154(b) by 0 days.

(21) Appl. No.: 09/449,922

(22) Filed: Dec. 2, 1999

Related U.S. Application Data

(63) Continuation of application No. PCT/SE98/01058, filed on Jun. 3, 1998.

(30) Foreign Application Priority Data

Jun. 4, 1997 (SE) .............................. 9702112

(51) Int. Cl.$^7$ ......................... G01N 33/53; G01N 33/48; G01N 27/00; G01N 27/26; C12M 3/00

(52) U.S. Cl. .................. 435/287.1; 435/7.1; 435/284.1; 435/288.3; 435/297.2; 436/63; 530/802; 422/82.01; 422/104; 204/400; 204/403

(58) Field of Search ............................... 435/7.1, 284.1, 435/287.1, 288.3, 297.2; 530/802; 422/82.01, 104; 436/63; 204/400, 403

(56) References Cited

U.S. PATENT DOCUMENTS

| 4,906,779 A | | 3/1990 | Weber et al. |
| 5,114,681 A | | 5/1992 | Bertoncini et al. |
| 5,208,145 A | * | 5/1993 | Rogers ........................... 435/6 |
| 5,460,782 A | * | 10/1995 | Coleman et al. ............ 422/100 |
| 5,597,699 A | | 1/1997 | Lanzara |

FOREIGN PATENT DOCUMENTS

| WO | WO90/04645 | 5/1990 |
| WO | WO93/24629 | 12/1993 |
| WO | WO94/20841 | 9/1994 |
| WO | WO96/10170 | 4/1996 |
| WO | WO96/13721 | 5/1996 |

OTHER PUBLICATIONS

Altria, K.D., et al., *Anal. Proc.,* "Measurement of Electro-endosmotic Flows in High–Voltage Capillary Zone Electro-phoresis," 23:453–454 (1986).

(List continued on next page.)

*Primary Examiner*—Bao-Thuy L. Nguyen
*Assistant Examiner*—Kartic Padmanabhan
(74) *Attorney, Agent, or Firm*—Edwards & Angell, LLP; David G. Conlin; Dianne M. Rees

(57) ABSTRACT

The invention provides a method for detection of receptor- or ion channel-modulators (e.g., antagonists, blockers, etc.). The method comprises fractionating a sample by using a liquid-based separation means (e.g., such as a capillary electrophoresis device), and feeding the fractions containing the modulators directly to a biosensor. The biosensor is activatable by a receptor agonist and produces a measurable response as a result of this activation. Preferably, the agonist is fed to the biosensor through the liquid-based separation means, together with fractions containing the modulators (e.g., antagonists or blockers). The presence of a modulator is detected by monitoring a change in the response of the biosensor, e.g., by measuring changes in electrical properties of the biosensor (such as through patch clamp analysis). In one aspect, the biosensor is periodically resensitized by delivering pulses of receptor agonist to the biosensor for short period of time which are separated by other periods when no agonist is delivered to the biosensor. The invention further provides a system for performing the method. The system facilitates sequential patch clamp recordings of cell-based biosensors.

1 Claim, 8 Drawing Sheets

OTHER PUBLICATIONS

Aram, J.A., et al., *J. Pharmacol. Ther.* "Neocortical Epileptogenesis in Vitro: Studies with N–Methyl–D–Aspartate, Phencyclidine, Sigma and Dextromethorphan Receptor Ligands," 248(1): 320–328 (1989).

Avila, L.Z., et al., *J. Med. Chem.*, "Use of Affinity Capillary Electrophoresis to Determine Kinetic and Equilibrium Constants for Binding of Arylsulfonamides to Bovine Carbonic Anyhydrase," 36:126–133 (1993).

Barnard, E.A. et al., *Proc. R. Soc. London Ser. B*, "Translation of exogenous messenger RNA coding for nicotinic acetylcholine receptors produces functional receptors for Xenopus oocytes," 215:241–246 (1982).

Baxter, G.T., et al., *Biochemistry*, "PKCε Is Involved in Granulocyte–Macrophage Colony–Stimulating Factor Signal Transduction: Evidence from Microphysiometry and Antisense Oligonucleotide Experiments," 31:19050–10954 (1992).

Benveniste, H. et al., *J. Neurochem.*, "Elevation of the Extracellular Concentrations of Glutamate and Aspartate in Rat Hippocampus During Transient Cerebral Ischemia Monitored by Intracerebral Microdialysis," 43(5):1369–1374 (1984).

Beohar, N., et al., *J. Biol. Chem.*, "Transcriptional Regulation of the Human Nonmuscle Myosin II Heavy Chain–A Gene," 273(15):9168–9178 (1998).

Bonnichsen, R., et al., *Zacchia*, "Identification of small amounts of barbiturate sedatives in biological samples by a combination of gas chromatography and mass spectrometry," 6:371–385 (1970).

Bouvier, C., et al., *J. Recept. Res.*, "Dopaminergic Activity Measured in $D_1$– and $D_2$–Transfected Fibroblasts by Silicon–Microphysiometry," 13(1–4):559–571 (1993).

Carroll, C.D., et al., *Adv. Exp. Med. Biol.*, "Screening Aspartyl Proteases with Combinatorial Libraries," 436:375–380 (1998).

Chu, Y–H, et al., *J. Med. Chem.*, "Use of Affinity Capillary Electrophoresis To Measure Binding Constants of Ligands to Proteins," 35:2915–2917 (1992).

Clackson, T., et al., *Nature*, "Making antibody fragments using phage display libraries," 352:624–628 (1991).

Cohen, A.S. et al., *Chromatographia*, "High–Performance Capillary Electrophoresis Using Open Tubes and Gels," 24:15–24 (1987).

Cohen, A.S. et al., *J. Chromatogr.*, "High Performance Sodium Dodecyl Sulfate Polyacrylamide Gel Capillary Electrophoresis of Peptides and Proteins," 397:409–417 (1987).

Colquhoun, D., et al., *Proc. R. Soc. Lond. B. Biol. Sci.*, "On the stochastic properties of single ion channels," 199:231 (1981).

Coyle, J.T., et al., *Science*, "Oxidative Stress, Glutamate, and Neurodegenerative Disorders," 262:689–695 (1993).

Everaerts, F.M., et al., *J. of Chrom. Library*, "Isotachophoresis: Theory, Instrumentation and Applications," Elsevier, Amsterdam, 6 (1976).

Ferry, G., et al., *Mol. Divers.*, "Selection of a histidine–containing inhibitor of gelatinases through deconvolution of combinatorial tetrapeptide libraries," 2:135–146 (1996).

Gomez, F.A., et al., *Anal. Chem.*, "Determination of Binding Constants of Ligands to Proteins by Affinity Capillary Electrophoresis: Compensation for Electroosmotic Flow," 66:1785–1791 (1994).

Gurdon, J.B., et al., *Nature*, "Use of Frog Eggs and Oocytes for the Study of Messenger RNA and its Translation in Living Cells," 233:177–182 (1971).

Hagberg, H. et al., *J. Cereb. Blood Flow Metab.*, "Ischemia–Induced Shift of Inhibitory and Excitatory Amino Acids from Intra– to Extracellular Compartments," 5(3):413–419 (1985).

Hamill, O.P., et al., *Pflüg. Arch.*, "Improved Patch–Clamp Techniques for High–Resolution Current Recording from Cells and Cell–Free Membrane Patches," 391:85–100 (1981).

Hirst, R.A., et al., *J. Neurochem.*, "Effects of C–Terminal Truncation of the Recombinant δ–Opioid Receptor on Phospholipase C and Adenylyl Cyclase Coupling," 70(6):2273–2278 (1998).

Hjertén, S., et al., *Protides Biol. Fluids,* "Analytical and Micropreparative High–Performance Electrophoresis," 33:537–540 (1985).

Hjertén, S., et al., *J. Chromatogr.*, "Micropreparative Version of High–Performance Electrophoresis: The Electrophoretic Counterpart of Narrow–Bore High–Performance Liquid Chromatography," 327:157–164 (1985).

Honoré, T., et al., *Science*, "Quinoxalinediones: Potent Competitive Non–NMDA Glutamate Receptor Antagonists," 241:701–703 (1988).

Hosford, D.A. et al., *Soc. Neurosci. Abstr.* "Excitatory Amino Acid (EEA) Receptor Binding in Epileptic Human Hippocampi," 15:1163 (1989).

Houghten, R.A., et al., *Biotechniques*, "The Use of Synthetic Peptide Combinatorial Libraries for the Identification of Bioactive Peptides," 13(3):412–421 (1992).

Houghten, R.A., *Nature*, "Generation and use of synthetic peptide combinatorial libraries for basic research and drug discovery," 354:84–86 (1991).

Hsieh, S., et al., *Anal. Chem.*, "Separation and Identification of Peptides in Single Neurons by Microcolumn Liquid Chromatography—Matrix–Assisted Laser Desorption/Ionization Time–of–Flight Mass Spectrometry and Postsource Decay Analysis," 70(9):1847–1852 (1998).

Huse, W., *Ciba Found Symp.*, "Construction of combinatorial antibody expression libraries in *Escherichia coli*," 159:91–102 (1991).

Jacobson, I., *Neurosci. Res. Comm.*, "Noise Analysis of Currents Activated by Excitatory Amino Acids in Freshly Isolated Neurones from the Olfactory Bulb of the Rat," 8(1):11–19 (1991).

Jacobson, I., et al., *Neurosci. Res. Comm.*, "Whole–Cell Currents Activated by N–Methyl–D–Aspartate in Freshly Isolated Neurones from the Olfactory Bulb of the Rat," 10(3):177–185 (1992).

Jiráček, J., *J. Biol. Chem.*, "Development of Highly Potent and Selective Phosphinic Peptide Inhibitors of Zinc Endopeptidase 24–15 Using Combinatorial Chemistry," 270(37):21701–21706 (1995).

Jorgenson, J.W., *Trends Anal. Chem.*, "Zone electrophoresis in open–tubular capillaries," 3(2):51–54 (1984).

Jorgenson, J.W., et al., *J. High Resolut. Chromatogr. Comm.*, "Capillary Zone Electrophoresis: Effect of Physical Parameters on Separation Efficiency and Quantitation," 8:407–411 (1985).

Kang, A.S., et al., *Proc. Natl. Acad. Sci. USA*, "Linkage of recognition and replication functions by assembling combinatorial antibody fab libraries along phage surfaces," 88:4363–4366 (1991).

Katz, B., and Thesleff, S., *J. Physiol., London,* "A Study of the 'Desensitization' Produced by Acetylcholine at the Motor End–Plate," 138:63–80 (1957).

Knox, J.H., *Chromatographia,* "Thermal Effects and Band Spreading in Capillary Electro–Separation," 26:329–336 (1988).

Li, Z., et al., *Eur. J. Biochem.,* "Functional expression of recombinant N–methyl–D–apartate receptors in the yeast *Saccharomyces cerevisiae,*" 252:391–399 (1998).

McComb, M.E. et al., *J. Chromatogr. A,* "Sensitive high-resolution analysis of biological molecules by capillary zone electrophoresis coupled with reflecting time–of–flight mass spectrometry," 800:1–11 (1998).

McConnell, H.M., et al., *Science,* "The Cytosensor Microphysiometer: Biological Applications of Silicon Technology," 257:1906–1912 (1992).

Ostresh, J.M., et al., *Proc. Natl. Acad. Sci. USA,* "Libraries from libraries': Chemical transformation of combinatorial libraries to extend the range and repertoire of chemical diversity," 91:11138–11142 (1994).

Park, K., et al., *J. Membr. Biol.,* "Comparison of Voltage-–activated Cl$^-$ Channels in Rat Parotid Acinar Cells with CIC–2 in a Mammalian Expression System," 163:87–95 (1998).

Persson, M.A.A., et al., *Proc. Natl. Acad. Sci. USA,* "Generation of diverse high–affinity human monoclonal antibodies by repertoire cloning," 88:2432–2436 (1991).

Pinilla, C., et al., *Biomed. Pept. Proteins Nucleic Acids,* "Two Antipeptide Monoclonal Antibodies that Recognize Adhesive Sequences in Fibrinogen: Identification of Antigenic Determinants and Unrelated Sequences Using Synthetic Combinatorial Libraries," 1:199–204 (1995).

Raley–Susman, K.M., et al., *J. Neurosci.,* "Effects of Excitotoxin Exposure on Metabolic Rate of Primary Hippocampal Cultures: Application of Silicon Microphysiometry to Neurobiology," 12(3):773–780 (1992).

Sastry, L., et al., *Ciba Found Symp.,* "Screening combinatorial antibody libraries for catalytic acyl transfer reactions," 159:145–155 (1991).

Siesjö, B.K. et al., *J. Cereb. Blood Flow Metab.,* "Calcium Fluxes, Calcium Antagonists, and Calcium–Related Pathology in Brain Ischemia, Hypoglycemia, and Spreading Depression: A Unifying Hypothesis," 9(2):127–140 (1989).

Smart, T.G., *J. Physiol.,* "A Novel Modulatory Binding Site for Zinc on the Gaba$_A$ Receptor Complex in Cultured Rat Neurones," 447:587–625 (1992).

Sumikawa, K., et al., *Nature,* London, "Active multi–subunit ACh receptor assembled by translation of heterologous mRNA in Xenopus oocytes," 292:862–864 (1981).

Tawfik, D.S. et al., *Proc. Natl. Acad. Sci. USA,* "catELISA: A facile general route to catalytic antibodies," 90:373–377 (1993).

Taylor, G.W. et al., *Br. J. Clin. Pharmacol.,* "Excursions in biomedical mass spectrometry," 41:119–126 (1996).

Terabe, S., et al., *Anal Chem.,* "Band Broadening in Electrokinetic Chromatography with Micellar Solutions and Open–Tubular Capillaries," 61:251–260 (1989).

Tretyakova, N.Y., et al., *J. Mass Spectrom.,* "Quantitative Analysis of 1,3–Butadene–induced DNA Adducts In vivo and In vitro using Liquid Chromatography Electrospray Ionization Tandem Mass Spectrometry," 33:363–376 (1998).

Tsuda, T., et al., *J. Chromatogr.,* "Microcapillary Liquid Chromatography Osmosis Flow Using a UV Detector," 248:241–247 (1982).

Tu, J., et al., *Clin. Chem.,* "Combinatorial search for diagnostic agents: Lyme antibody H9724 as an example," 44(2):232–238 (1998).

Yeh, G–C. et al., *Proc. Natl. Acad. Sci. USA,* "N–Methyl-D–aspartate receptor plasticity in kindling: Quantitative and quantitative alterations in the N–Methyl–D–aspartate receptor–channel complex," 86:8157–8160 (1989).

Cecilia Farre, et al, "Screening of Ion Channel Receptor Agonists Using Capillary Electrophoresis–Patch Clamp Detection with Resensitized Detector Cells", Analytical Chemistry, vol. 73, No. 6, pp. 1228–1233, Mar. 15, 2001.

Harvey Fishman, et al, "Identification of receptor ligands and receptor subtypes using antagonists in a capillary electrophoresis single–cell biosensor separation system", Proc Natl. Acad. Sci. USA, vol. 92, pp. 7877–7881, Aug. 1995.

Harvey Fishman, et al, "Cell–to–Cell Scanning in Capillary Electrophoresis", Analytical Chemistry, vol. 68, No. 7, pp. 1181–1186, Apr. 1, 1996.

* cited by examiner

Absorbance Detection

Patch - Clamp Detector

Interlocked Pulsed Patch Clamp Detector

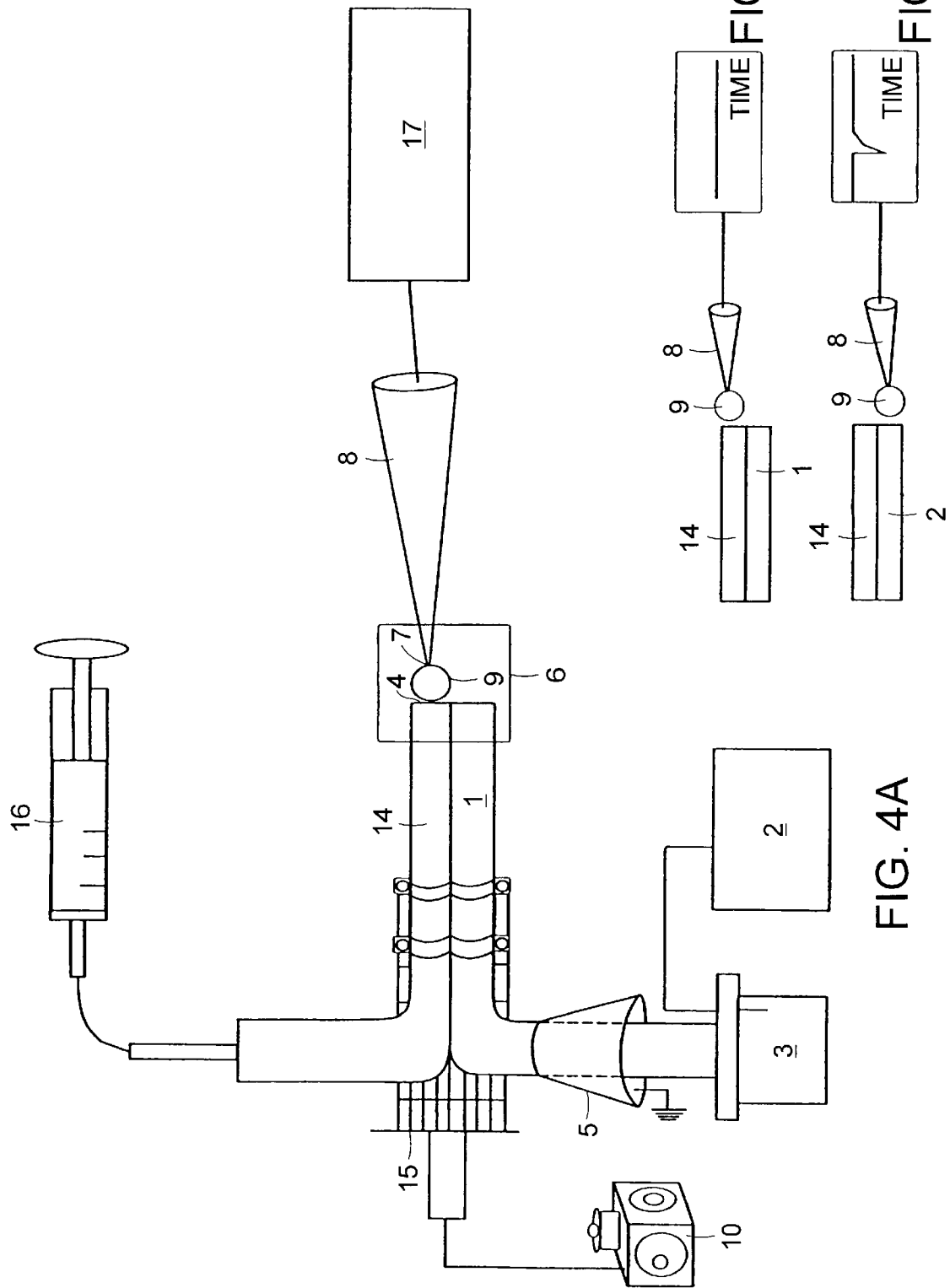

DETECTION OF BIOLOGICALLY ACTIVE MOLECULES BY USE OF PRE-ACTIVATED CELL-BASED BIOSENSORS IN LIQUID-BASED SEPARATION SYSTEMS

This is a continuation of International Application No. PCT/SE98/01058, filed Jun. 3, 1998, that designates the United States of America and with claims priority from Swedish Application No. 9702112-5, filed Jun. 4, 1997.

FIELD OF THE INVENTION

The present invention relates to a method and an apparatus for detection of endogenous and synthetic receptor antagonists and receptor modulators, such as e.g. drugs and pharmaceutically active substances. More specifically, the present invention relates to a method and an apparatus based on the use of a miniaturized liquid-based separation technique coupled to a biosensor activated by a receptor agonist and thus giving rise to a measurable response that is affected in a measurable way by the receptor antagonist to be detected.

BACKGROUND OF THE INVENTION

Biologically active compounds generally lack features enabling sensitive detection thereof by conventional techniques, and their roles in biochemical and physiological processes are therefore often difficult to elucidate.

The detection of biologically active compounds is of particular interest in the pharmaceutical field, e.g. during development of new drugs. Since many native and synthetic substrates constituting commercial drugs act as inhibitors of dysfunctional events in the human body, it is of importance to find systems that enable screening or detection of molecules with that mode of action.

In recent years, there has been an exponential increase in the number of compounds which are interesting for screening. Synthetic libraries from drug companies and natural products have been some of the sources of these compounds. The compounds origin from a broad spectrum of different organisms, such as bacteria, insects, plants and marine organisms. This, together with the introduction of combinatorial libraries for the manufacturing of several thousands of compounds have led to a great demand for new screening techniques which are faster and more selective than the ones used today. Known methods used for drug screening are generally based on pure chemical binding between compounds extracted from, for example, natural products and target molecules, such as receptors, enzymes or nucleic acids. The target molecules can also be included in biological systems, such as living cells, where the merits of chemical recognition and biological amplification are combined.

The use of specific target molecules for the evaluation of a compound's biological potential is based on the creation of systems of biological relevance for the analyzed compound. Strategies in this field often include expression of cloned cDNA in different cell systems for the production of a functional target molecule in its natural environment.

There are also examples of screening systems which are based on cell effects where the response cannot be traced to a single target molecule.

Several different techniques are presently used for biological screening and characterization of potential drugs, and some examples of these techniques are given below.
Microphysiometry During the growth of a typical biological cell, carbon-containing nutrients such as glucose are taken up and acidic metabolic products such as lactic acid are released. In microphysiometry these changes in metabolic rate are recorded as changes in the rate of acidification of the medium surrounding the cells (see e.g. Raley-Susman, K. M., et al., J. Neurosci. 12:773, 1992; Baxter, G. T., et al., Biochemistry 31:10950, 1992; Bouvier, C., et al., J. Recept. Res. 13:559, 1993; and McConnell, H. M., et al., Science 257:1906, 1992). Virtually any molecule that affects the cell can be detected by this method. Such molecules include neurotransmitters, growth factors, cytokines and so forth. The microphysiometry is unable to distinguish between different antagonists acting on the same receptor system and can therefore not be used for binary or more complex solutions of such agents. Other drawbacks of this system are the low-level detection, measuring changes in pH is far less selective than measuring responses on the receptor level, and slow recovery rates.
Immunoassays This group of techniques is based on in vitro procedures for screening of specific antigens (see e.g. Tu, J., et al., Clin. Chem. 44:232, 1998; Pinilla, C., et al., Biomed. Pept. Proteins Nucleic Acids 1:199, 1995; Tawfik, D. S., et al., Proc. Natl. Acad. Sci. USA 90:373, 1993; and Houghten, R. A., et al., Biotechniques 13:412, 1992). Antibodies, often immobilized, are used as targets for antigens. The antigen-antibody interaction is detected by a second antibody, which is labeled by, e.g., a radioactive isotope. The problems with these immuno-based techniques are related to the difficulties in raising specific antibodies for small molecules that are identical or resemble endogenous compounds. Another problem is related to the handling of radioactive substances.
Use of Combinatorial Libraries Synthetic combinatorial libraries have proven to be a valuable source of diverse structures useful for large-scale biochemical screening (see e.g. Sastry, L., et al., Ciba Found Symp. 159:145, 1991; Huse, W., Ciba Found Symp. 159:91, 1991; Persson, M. A., et al., Proc. Natl. Acad. Sci. USA 88:2432, 1991; Kang, A. S., et al., Proc. Natl. Acad. Sci. USA 88:4363, 1991; Houghten, R. A., et al., Nature 354:84, 1991; Clackson, T., et al, Nature 352:624, 1991; and Ostresh, J. M., et al., Proc. Natl. Acad. Sci. 91:11138, 1991). The libraries are generated by a combination of solution and solid-phase chemistries and are cleaved off the solid-support for screening. When mixtures of compounds are screened, however, the possibility exists that the most active compound will not be identified.
Separation Techniques Coupled to Mass Spectrometry Separation techniques such as liquid chromatography, gas chromatography and capillary electrophoresis coupled to mass spectrometry or tandem-mass spectrometry create analytical systems available for structure evaluation (see e.g. Hsieh, S., et al., Anal. Chem. 70:1847, 1998; Tretyakova, N. Y., et al., J. Mass. Spectrom. 33:363, 1998; Bonnichsen, R., et al., Zacchia 6:371, 1970; Taylor, G. W., et al., Br. J. Clin. Pharmacol. 42:119, 1996; and McComb, M. E., et al., J. Chromatogr. A 800:1, 1998). Mass spectrometry gives information about the molecular weight of the analyzed molecule. With refined and controlled fragmentation of large molecules it is also possible to extract information about the sequence.
Enzyme Assays Using Proteases Many proteases have become targets for drug discovery (see e.g. Carroll, C. D., et al., Adv. Exp. Med. Biol. 436:375, 1998; Ferry, G., et al., Mol. Divers. 2:135, 1997; and Jiracek, J., et al., J. Biol. Chem. 270:21701, 1995), from viral proteases required for the generation of active viral proteins to mammalian proteases that process pro-hormones to their active mature forms. Assays have been developed in bacterial systems to screen for compounds that inhibit protease activity. Most of these involve the co-expression of both the protease and a target reporter gene (the gene that encoded the protein which creates a measurable effect) in the same cell. A number of in vitro biochemical assays have also been developed. In most of these cases, a peptide containing the protease cleavage site is labeled at one end using either a radioactive or a fluorescent tag. The other end of the peptide molecule is adhered to a plate or a bead. In the presence of an active protease, the peptide is cleaved and the labeled end is released. The loss of signal from the labeled end of the peptide molecule after washing reflects the activity of the protease and can be easily monitored. For detection of protease inhibitor the grade of maintenance of the signal can instead be measured. These assays are, however, often time consuming since they involve genetic engineering.

A significant limitation of the above mentioned methods is the capacity; the number of compounds that can be rapidly evaluated is extremely low. Alternative methods for high through-put screens are needed.

Another major disadvantage of these known biological screening systems is that they involve extensive multistep purification and isolation of the compounds which are to be tested.

Capillary-based separation methods for identifying bioactive analytes in a mixture have earlier been described in WO 96/10170 (PCT/US95/12444). The methods described herein is however not fully satisfying for detection of antagonists. In the application detection of antagonists is mentioned. However, it seems that the agonist needed for detection of antagonists is then either included in the bathing solution or fed to the cell by a second capillary or tube system. A major drawback with this solution is that the agonist would immediately dissipate from the surface of the cell-based biosensor when the separation process is started. This eliminates the effect of pre-activation which is necessary for accurate biosensor-detection of antagonists.

SUMMARY OF THE INVENTION

The disadvantages of the above mentioned methods for drug screening can be eliminated with the method according to the present invention.

The present invention provides methods and apparatus for detection of biologically active analytes separated by liquid-based separation means. The analytes or antagonists to be detected act can act as ligands, which means that they can bind to a specific receptor or receptors. The method employs cell-based biosensors expressing specific receptors to serve as ligand detectors. An important feature of the invention is that the receptor, comprising the functional unit of the detector, is preactivated by constantly including a receptor-specific agonist or modulator into the liquid-based separation means. Analytes, such as antagonists, is detected in that they modulate or inhibit the pre-activated receptor response. The use of a pre-activated or constantly activated biosensor is one of the most important characteristics of the present invention.

Thus, the present invention relates to a method for detection of at least one receptor antagonist and/or at least one receptor modulator, comprising the following steps:

a sample containing the receptor antagonist or modulator is fractionated by use of a liquid-based separation means, (II) a fraction containing the receptor antagonist or modulator is fed directly to a biosensor (9) which is activated by an appropriate receptor agonist and, as a result of this activation, is generating a measurable response, said agonist being fed to the biosensor through the liquid-based separation means together with the antagonist or modulator, said activation of the biosensor being pulsed by delivery of the receptor agonist to the biosensor for short period of times, said periods being separated by other periods when no agonist is delivered to the biosensor, and (III) the change of the response resulting from deactivation of the receptor agonist-activated biosensor by the receptor antagonist or modulator is measured. The present invention also relates to an apparatus for detection of a receptor antagonist comprising a capillary electrophoresis separation capillary containing an electrolyte supplemented with an appropriate receptor agonist, the sample inlet part of which is connected to a high-voltage power supply through a buffer vial containing a buffer supplemented with an appropriate receptor agonist and the grounded outlet part of which ends close to a patch-clamped biosensor that is activated by the receptor agonist and deactivated by the fractionated antagonist; the apparatus further comprising a patch clamp electrode and means to record currents detected by the patch clamp electrode.

The method and the apparatus according to the present invention enables a one-step fractionation immediately followed by detection. This is a big advantage compared to known techniques which involves several separation steps.

The present invention also relates to an apparatus and method for better resolution of the separated analytes or antagonists due to a periodic resensitisation of the biosensor by an pulsed flow system.

The methods and the apparatuses according to the invention have a variety of uses. For example, they are well-suited for drug screening since many drugs or pharmaceutically active components are receptor antagonists or receptor modulators, but they can also be used for applications in other areas such as environmental, food, and cosmetic industries.

When the method or the apparatus according to the invention is used for screening of antagonists or drugs they provide a number of advantages over methods according to prior art. Since cell biosensors of the type described herein by themselves are not particularly useful at identifying antagonists or drugs acting as inhibitors in a mixture of antagonists or drugs, it is a great advantage to use the method according to which they are pre-activated by a selective agonist which is incorporated into the running buffer in the liquid-based separation means. An advantage of this system is that the state of the biosensor, that is the degree of receptor activation, is known through this continuous activation, by an agonist. An another significant advantage of the present invention is that long-time exposure of the cell by agonist or antagonist can be avoided by displacement of the cell from the outlet of the liquid-based separation means. This is in contrast to keeping the concentration of the agonist at a high level in the buffer solution in the Petridish, as described in the above mentioned patent application PCT/US95/12444. The fact that the agonist according to the present invention is present in the liquid-based separation means where the separation of the antagonist takes place provides a very important advantage compared to the methods described in WO 96/10170 since this results in a pre-activation of the biosensor enabling accurate detection of antagonists.

The features of the invention will be evident from the following description and the appended claims.

BRIEF DESCRIPTIONS OF THE DRAWINGS

The invention will now be described in further detail hereinafter with reference to the accompanying drawings on which:

FIGS. 1A–C shows, for comparison, absorbance detection, patch clamp detection and i pulsed patch-clamp detection, coupled to capillary electrophoresis. FIG. 1A shows the separation and detection of analyte 1 and analyte 2, with similar migration times, by absorbance detection in capillary electrophoresis. The recorded trace gives gaussian distributed and overlapping peaks. FIG. 1B shows capillary electrophoresis patch clamp detection of the same separation of analyte 1 and analyte 2, as in FIG. 1A. Notable is that only analyte 1 is detected due to desensitisation. FIG. 1C shows a theoretical prediction of that repeated resensitisation of the detector by pulsing gives an increased resolution in CE-PC detection of analyte 1 and analyte 2.

FIG. 2 shows a preferred embodiment of the apparatus according to the invention, namely a capillary electrophoresis-patch clamp detection system.

FIGS. 3A–B shows an enlarged part of the capillary electrophoresis-patch clamp detection system according to FIG. 2. FIG. 3A shows the electrophoresis capillary. The capillary, into which a receptor antagonist has been injected, is filled with a receptor agonist-supplemented buffer and its flow is directed onto the surface of a patch-clamped cell. FIG. 3B shows the same capillary and the same patch-clamped cell at a later point of time when the receptor antagonists have migrated through the entire length of the capillary and started to antagonize the binding of receptor agonists.

FIGS. 4A–B show a model of a device constructed for switching between superfusion and electrophoresis. FIG. 4A shows the device consisting of two fused silica capillaries which are mounted in parallel. The cell, which is attached to the patch clamp electrode, is placed in front of one of the two capillaries by a micromanipulator. FIG. 4B illustrates how the receptors at the cell-surface are resensitised due to superfusion of the cell by a physiological buffer when the cell is in position one. FIG. 4C illustrates how electrophoretically separated analytes are detected by means of patch clamp when the cell is in position two.

FIGS. 5A and B show a schematic drawing presenting a second strategy for resensitisation of a receptor system used in patch clamp detection. This superfusion system comprises a micropipette which is placed close to the cell in the vicinity of the electrophoresis capillary outlet. A buffer flow from the micropipette is applied leading to washing of the analytes from the surface of the patch clamped cell. Dissociation of the analytes from the receptors makes the cell detector resensitised. When the buffer flow is interrupted the electrophoretically separated analytes are able to bind to the receptors at the cell surface and an ion-channel mediated current is recorded by the patch-clamp amplifier system.

FIGS. 6A–C shows electropherograms illustrating controls and detection of $Mg^{2+}$ ions. FIG. 6A illustrates a control trace showing activation of NMDA receptors by NMDA and glycine, FIG. 6B illustrates a blocked response of the NMDA receptor-mediated current by separated $Mg^{2+}$ ions. FIG. 6C shows a control-trace presenting the unaffected NMDA receptor response after injection of HEPES-saline containing NMDA and glycine.

DETAILED DESCRIPTION OF THE INVENTION

Figure 1A:
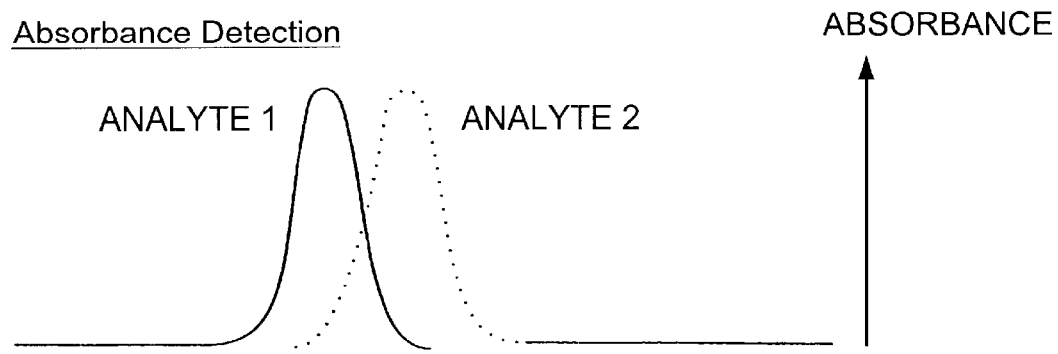

Below are definitions and explanations of several terms used in the description and in the appended claims.

The term "liquid-based separation means" refers to any method or apparatus for separation of a mixture of analytes or antagonists that are dissolved in a physiologically buffer, solution or any other liquid. Examples could be variations of capillary electrophoresis, as capillary zone electrophoresis, capillary gel electrophoresis, micellar electrokinetic capillary electrochromatography, capillary isolectric focusing, capillary isotachophoresis, and affinity capillary electrophoresis, as well as variations of micro liquid chromatography, such as open tube liquid chromatography.

The term "cell-based biosensor" refers to an intact cell, a part of an intact cell (such as a membrane patch), or a cell in electrical communication with a patch-clamp glass-electrode or another material, a patch or piece of a cell-membrane which is in electrical communication with a solid material as, for example, a glass capillary, plastic or silicon surface or anything related.

The term "target molecule" refers to a macromolecule composed of a protein, glycoconjugates or lipids, which interacts with or binds to a ligand, analyte, an antigen or anything related. A target molecule can be a receptor, an antibody, an enzyme, or anything related. The binding of an analyte, ligand or antigen may trigger a physiological relevant process which signals the ligand's or the analyte's biological activity. A target molecule may be associated to an artificial or a natural lipid monolayer or bilayer membrane, such as a plasma membrane, mitochondrial membrane or golgi membrane.

The term "receptor" refers to a macromolecule capable of specifically interacting with a ligand molecule. Receptors may be associated with lipid bilayer membranes, such as the extracellular, golgi or nuclear membranes, and/or be present as free or associated molecules in the cell's cytoplasm. Further, receptors may be either native to the cell biosensor, i.e. normally expressed by the cell from which the cell biosensor is derived, or recombinant, i.e. expressed in transfected cells or Xenopus oocytes.

The term "ligand" refers to a molecule which binds to a receptor which either becomes activated or inactivated. Ligands can act on the receptor as agonists or antagonists or by modulating the response of the receptor by other agonists or antagonists. Binding of the ligand to the receptor is typically characterized by a high binding affinity.

As used in the description below and in the claims, the term "receptor antagonist" relates to receptor antagonists as well as to receptor modulators and receptor blockers. Below, the term antagonist is used in the singular form, but the invention is of course also applicable to mixtures of different antagonists and/or receptor modulators.

To decrease the time needed for screening and to minimize the number of purification steps, screening of receptor antagonists and receptor modulators using biosensors, which include target molecules (i.e. receptors), is according to the present invention coupled, preferably on-line, to a miniaturized liquid-based separation technique. This combination of a separation technique and an on-line biosensor is based on a highly efficient one-at-a-time receptor antagonist delivery to the biosensor for functional detection.

The miniaturized liquid-based separation means used according to the present invention are suitable for separating ligand analytes in picoliter and nanoliter volumes. Preferably, the miniaturized liquid-based separation means used is capillary electrophoresis. The capillary electrophoresis can e.g. be any different mode of capillary electrophoresis known in the art, such as capillary zone electrophoresis, CZE (see e.g. Jorgenson, J. W., Trends Anal. Chem. 3:51, 1984, and Altria, K., et al., Anal. Proc. 23:453, 1986), capillary gel electrophoresis, CGE (see e.g. Hjerten, S., et al., J. Chromatogr. 327:157, 1985; Hjerten, S., et al., Protides Biol. Fluids 33:537, 1985; Cohen, A. S., et al, Chromatographia 24:14, 1987; and Cohen, A. S., et. al., J. Chromatogr. 397:409, 1987), micellar electrokinetic capillary electrochromatography, MECC (see e.g. Terabe, S., et al., Anal. Chem. 61:251, 1989, and Tsuda, T., et al., J. Chromatogr. 248:241, 1982), capillary elect rochromatography, CEC (see e.g. Knox, J. H., Chromatographia 26:329, 1988, and Jorgenson, J. W., et al., J. High Resolut. Chromatogr. Chromatogr. Commun. 8:407, 1985), capillary isotachophoresis, CIPT (see e.g. Everaerts, F. M., et al, Isotachophoresis: Theory. Instrumentation. and Application, Elsevier, Amsterdam, 1976, and Bocek, P., et al., Anal. Isotachophoresis, VCH Verlagsgesellschaft, Weinhein, 1988), or affinity capillary electrophoresis, ACE (see e.g. Chu, Y-H, et al., J. Med. Chem. 35:2915, 1992; Avila, L. Z., et al., J. Med. Chem. 36:126, 1993; and Gomez, F. A., et al., Anal. Chem. 66:1785, 1994).

In its simplest and most common embodiment capillary electrophoresis is a miniaturized separation technique that fractionates chemical species on the basis of differences in their ratios of electrical charge-to-frictional drag in a solution. Since different molecules have different charge-to-frictional drag ratios, separated components migrate at characteristic rates, making identification possible. With capillary electrophoresis it is possible to separate complex chemical mixtures with high efficiency (up to $10^6$ theoretical plates) in typically less than 20 minutes. Since capillary electrophoresis handles samples down to $10^{-18}$ liter, it is well suited for micro- and nanotechnology applications.

In its simplest and most common embodiment, a capillary electrophoresis system consists of a narrow-bore (inner diameter 5–75 μm fused-silica capillary (usually with a length of 20 to 100 cm) filled with an electrolyte solution. The ends of the capillary are placed in electrolyte-containing reservoirs having either a cathode or an anode connected to a high-voltage source. When an electrical field is applied across the solution-filled fused silica capillary, a layer of mobile charge that accumulates along the counter-charged fused silica surface induces electroosmosis (bulk solution flow). Under typical operating conditions for capillary electrophoresis this sheath of ions is positively charged, and consequently, drags bulk solution from the anode to the cathode. A practical result of electroosmosis flow is that during a separation in free-solution capillary electrophoresis, all species—whether possessing positive, neutral, or negative charge—can be made to migrate in the same direction past a single detector.

The biosensor used according to the present invention is preferably an eukaryotic or a prokaryotic cell containing specific receptors, a confluent layer of such cells, a part of a cell membrane containing specific receptors or a cluster of cells containing specific receptors. It is also possible to use a detector based on receptors inserted into or on liposomes, lipid films or other materials as a plastic surface or any related material.

The cells used for the biosensor, including a target molecule or a recombinantly expressed target protein, preferably a receptor, can be human, bacterial and/or yeast cells. Mammalian tissue cultured cells such as Chinese hamster ovary (CHO) cells, NIH-3T3 and HEK-293 cells, for example, are especially advantageous as cell-based biosensors expressing recombinant target molecules, in that they provide an environment that is similar to the milieu of the natural human cells (see e.g. Beohar, N., et al., J. Biol. Chem. 273:9168, 1998; Park, K., et al., J. Membr. Biol. 163:87, 1998; and Hirst, R. A., et al., J. Neurochem. 70:2273, 1998). To a great degree permeability, post-translational processing, signalling and coupling to other cellular factors in these cells are similar to these processes in most mammalian cells.

Another cell-system frequently used for expression of recombinant proteins is yeast (see e.g. Li, Z., et al., Eur. J. Biochem. 252:391, 1998). Yeast cells offer a number of advantages; they are well characterized, they are easy to manipulate genetically and fast growing. It has also been shown that they contain the machinery for post-translational modification and they possess intracellular signalling systems.

Furthermore, Gurdon and colleagues (see Gurdon, J. B., et al., Nature 233:177, 1971) opened a broad spectrum of possibilities for the study of the function of proteins by demonstrating the ability of Xenopus oocytes to synthesize exogenous proteins when injected with mRNA. The oocyte-model is a particularly attractive approach to the investigation of the structure-function relations of membrane proteins. Consequently, expression of functional receptors for neurotransmitters and ion-channels were demonstrated in oocytes in the beginning of the 1980s (see Sumikawa, K., et al., Nature, London 292:862, 1981, and Barnard, E. A., et al., Proc. R. Soc. London Ser. B 215:241, 1982).

Thus, living cells used as biosensors are particularly advantageous because of the physiological and functional information which can be extracted from a receptor-induced response.

As stated above, the present invention involves the use of receptor agonists making it possible to detect receptor antagonists. Nearly all cells possess on their surface a wide range of various receptors specific for appropriate agonists as well as antagonists. When binding a specific agonist, the receptor is activated and undergo a conformational change which triggers a cellular response.

These receptors have evolved their specificity during billions of years, which makes them very suitable as highly specific functional units in biosensors. Glutamate receptors, for example, play a crucial role in neurotransmission; the formation of neuronal circuits, in synaptogenesis and synaptic plasticity, including long-term potentiation (LTP) and long-term depression (LTD). Excessive activation of glutamate receptors is also thought to contribute to the neurodegeneration which takes place in a wide range of neurological insults such as brain ischemia (see e.g. Beneviste, H, et al., J. Neurochem. 43:1369, 1984, and Hagberg, H., et al., J. Cereb. Blood Flow Metab. 5:413, 1985) and epilepsy (see e.g. Aram, J. A., et al., J. Pharmacol. Exp. Ther. 248:320, 1989; Yeh, G. C., et al., Proc. Natl. Acad. Sci USA 86:8157, 1989; and Hosford, D. A., et al., Soc. Neurosci. Abstr. 15:1163, 1989).

The roles of glutamate receptors are strongly coupled to their ion-permeability properties, both in the normal and dysfunctional brain. Their selective permeability to $Na^+$, $K^+$ and $Ca^{2+}$ makes them mediators of synaptic transmission in many neurons of the central nervous system (CNS). A key event in glutamate induced cell death, for example, is increased intracellular $Ca^{2+}$ which generates free radicals and endonucleases (see e.g. Siesjö, B. K., et al., J. Cereb. Blood Flow Metab. 9:127, 1989, and Coyle, J. T., et al., Science 262:689, 1993) as well as transcriptional activation of specific "cell death". Thus naturally expressed receptors, as for example glutamate receptors, constitute excellent and selective detectors for detection and discovering of endogenous drug candidates, which may modulate or inhibit a wide range of receptor systems involved in the development of various diseases.

Bacteria such as *Escherichia coli, Bacillus* sp. and *Staphylococcus aureus* as well as yeast such as *Saccharomyces cerevisiae* provide alternative expression systems for cloned recombinant mammalian genes as well as microbial targets. Bacteria are genetically well characterized, have a short generation time, are easy to manipulate and inexpensive to grow. Thus these amplification systems provides a means of producing sufficient material of cDNA expressing a specific protein, which can be used in production of mRNA for injection in Xenopus oocytes or for transfection into mammalian tissue cultured cells.

The advantage with expressing recombinant genes in a cell-based biosensor used according to the invention is that the receptors in any of the cell- or cell membrane-based biosensors can be of any kind, e.g., voltage-gated ion channels, ligand-gated ion channels, metabotropic, hematopoetic, tyrosine-kinase-coupled receptors, etc. Biosensors, expressing recombinant receptors, can also be designed to be sensitive to drugs which may inhibit or modulate the development of a disease. This sensitivity of the biosensor will be governed by the role of a specific recombinant receptor in disease development. Thus, the choice of the biosensor is based on the receptor antagonist one wishes to screen. For example, it is possible to use liver cells in order to study receptor antagonists used in pharmaceuticals meant to affect the liver.

Since the receptor antagonist to be detected binds to the biosensor, e.g. containing cell receptors, without eliciting a response, the biosensor system needs to be activated, preferably constantly and preferably by a receptor agonist, in order to enable detection. The activation caused by the receptor agonist is changed, normally decreased, by the receptor antagonist and this change of the response is detectable.

As stated above, the biosensor is either preactivated or constantly activated by use of a receptor agonist. This receptor agonist is preferably included in the buffer solution in the liquid-based separation means.

The detection of the response generated by the activated biosensor and of the change of the response caused by the receptor antagonist to be detected are made by an appropriate technique depending on the type of the generated response. The response can e.g. be a transmembrane current measured by patch clamp or two-electrode voltage clamp, it can be fluorescence from voltage-sensitive dyes or it can be fluorescence from calcium-chelated fluorophores, such as Fura and Fluo-3 ($Ca^{2+}$ chelating dyes), which are included in measurements of intracellular calcium coupled to activation of metabotropic receptors in the cell membrane. The preferred detection technique according to the invention is patch clamp detection, and the generated response measurable is thus an electrical current.

Katz and Thesleff discovered that the macroscopic endplate conductance falls within a few seconds when acetylcholine (ACh) is added to an endplate (see Katz, B., and Thesleff, S., J. Physiol., London, 138:63, 1957). This process is called desensitisation. Desensitised channels were unresponsive to added ACh and recover their sensitivity only some seconds or even minutes after the removal of ACh. Generally, a broad range ligand-receptor interactions at cell surfaces, which triggers cell responses with varying characteristics, i.e. increased conductance across the cell membrane, activation of G-protein coupled intracellular cascade processes, phosphorylation of proteins or triggering of intracellular modulations of transcription, desensitise. Such receptor properties may cause problems in detecting antagonists with similar electrophoretic migration times when biological samples are separated and detected by the capillary electrophoresis-patch clamp (CE-PC) technique, where the receptor systems comprises the functional unit in the detector.

Figure 1B:
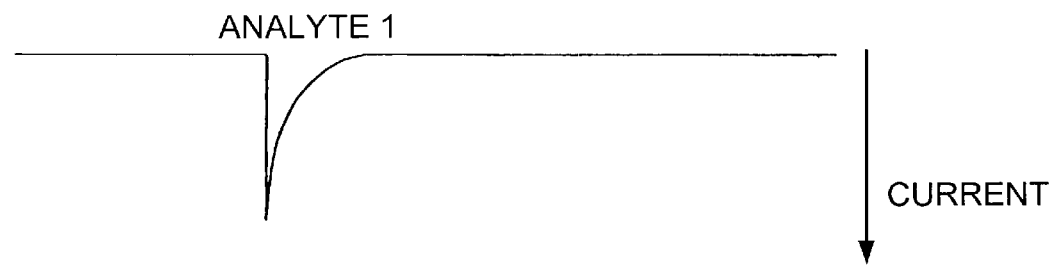
Figure 1C:
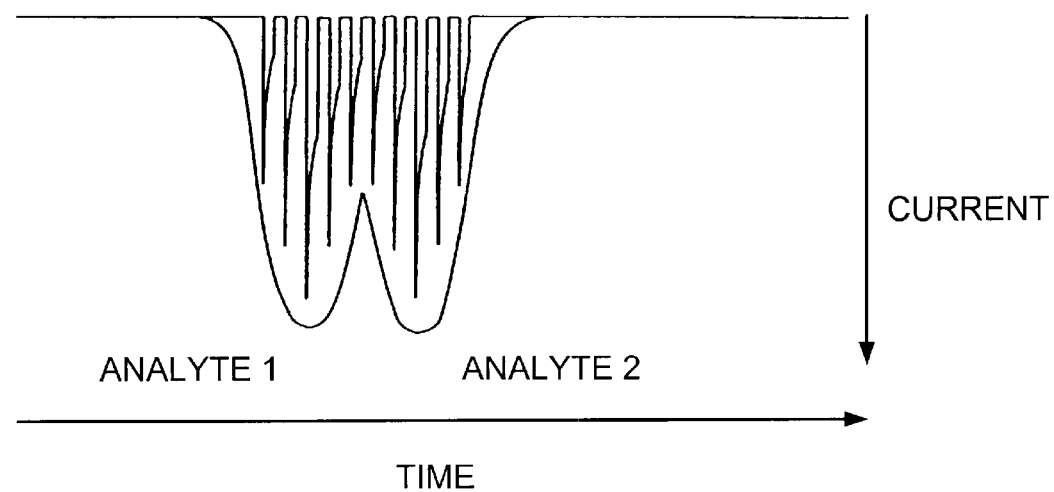

If two analytes (analyte 1 and analyte 2), as for example glutamate and aspartate, with similar migration times are separated and detected by a conventional detector such as an absorbance detector, the recorded trace will give gaussian distributed and overlapping peaks, as illustrated in FIG. 1A where the separation and detection of analyte 1 and analyte 2, with similar migration times, by absorbance detection in capillary electrophoresis is shown. Even if the responses are improperly resolved, the trace gives information about two existing compounds in the sample. However, if the same sample is separated by the CE-PC technique, analyte 2 will not be detected when both analytes activate the same desensitising receptor system. The receptor population will be activated and desensitised by analyte 1 before analyte 2 reaches the receptor surface leading to a single response in the electropherogram, as illustrated in FIG. 1B, where capillary electrophoresis-patch clamp detection of the same separation of analyte 1 and analyte 2 as in FIG. 1A is shown. Notable is that just analyte 1 is detected due to desensitisation. A solution to this problem involves pulsed resensitisation of the environment surrounding the cell-based detector. This will reactivate the receptors at a specific frequency due to repeated dissociation of the eluting analytes from the binding site of the receptor. The reactivation of the receptor population enables the analytes to repeatedly give desensitised responses which will be presented with a gaussian distribution, as illustrated in FIG. 1C., where a theoretical prediction of that repeated resensitisation of the detector by pulsing gives an increased resolution in CE-PC detection of analyte 1 and analyte 2 is shown. This will also improve the quantitative abilities of the technique.

Below, preferred embodiments of the present invention will be described.

According to the first preferred embodiment the miniaturized separation technique is capillary electrophoresis and the biosensor is a patch-clamped cell or part of a cell membrane, and the detection means are thus a patch clamp electrode.

According to the patch clamp technique, a cell or part of a cell is firmly attached by suction to the tip of a glass micropipette, or a patch clamp electrode, and manipulated to yield one of several desired configurations, i.e., outside-out, inside-out, or whole-cell recording modes. The outside-out and inside-out configurations refer to the word "patch", that is a small piece of a cell membrane which is attached to the tip of an electrode for recording of single ion-channel currents (see, e.g., Hamill, O. P., et al., Pflug. Arch. 391:85, 1981).

The patch clamp technique utilizes in its simplest embodiment a highly sensitive feedback current-to-voltage converter, which has the ability to measure sub-picoampere currents. The measuring principle of patch clamp relies on the fact that the ionic flow across a cell membrane can be measured as an electrical current if the membrane potential is held constant, typically for neuronal cells in the range −30 to −90 mV.

There are three main reasons to use the patch clamp technique to measure small currents crossing the cell-membrane:

(1) Clamping the voltage eliminates the capacitive current, except for a brief time following a step to a new voltage.

(2) Except for the brief charging time, the currents that flow are proportional only to the membrane conductance, i.e. to the number of open ion-channels.

(3) If ion-channel gating is determined by the transmembrane voltage alone, voltage clamp offers control over the key variable that determines the opening and closing of ion channels.

Figure 2:
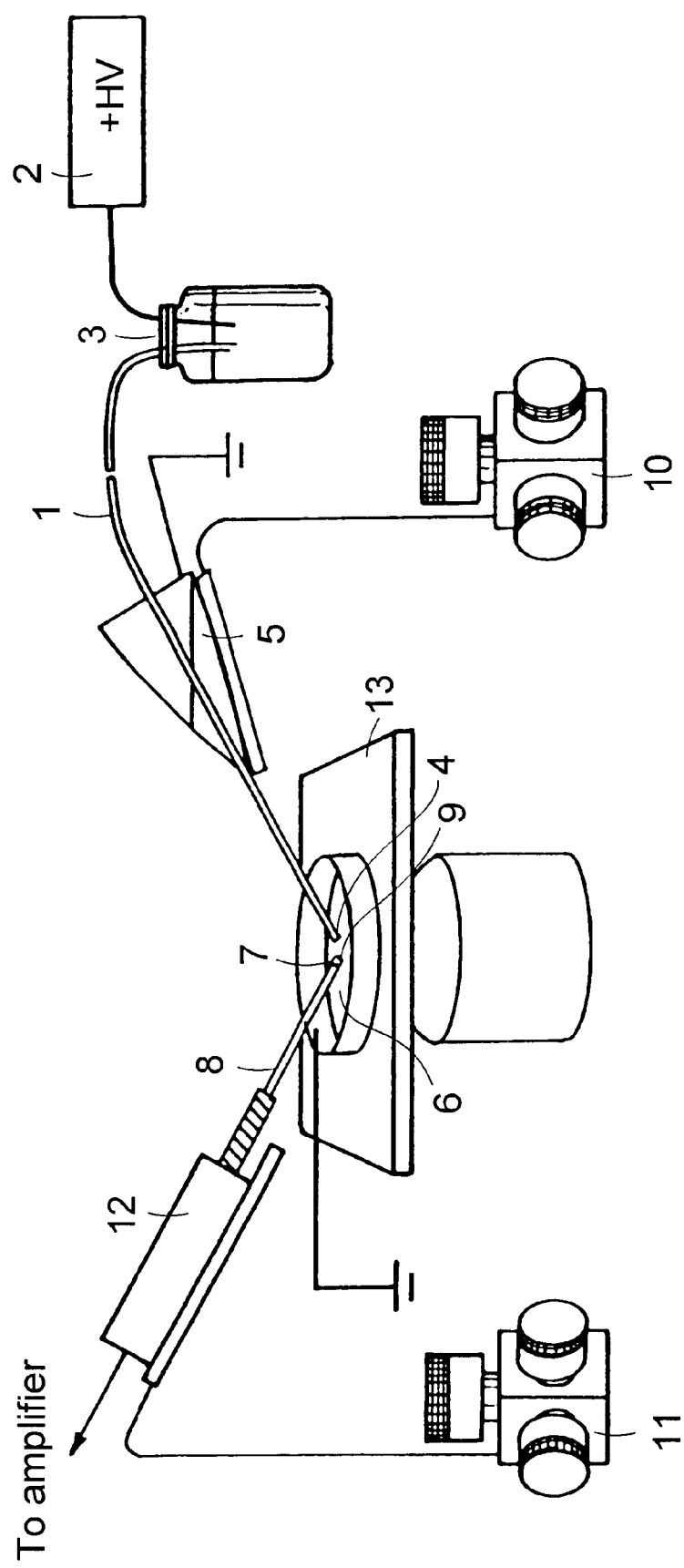

A preferred embodiment of the apparatus according to the present invention is shown in FIG. 2. The inlet end, i.e. the sample injection end, of a fused silica capillary electrophoresis separation capillary 1 is connected to a high-voltage power supply 2, preferably a positive high-voltage power supply, through a buffer vial 3. The buffer vial 3 is preferably housed in a polycarbonate holder equipped with a safety interlock to prevent electric shock. The capillary is grounded, e.g. approximately 5 cm above the outlet 4. The grounding can be accomplished by use of another buffer vial 5. The outlet 4 of the capillary 1 is positioned in a cell bath 6. The cell bath 6 contains the same media as the one used as electrolyte in the capillary electrophoresis capillary 1 with one exception—the media in the electrophoresis capillary 1 also comprises agonists which is lacking in the media in the cell bath. The same media as used in the cell bath is also used in the inlet buffer vial 3 and in the buffer vial 5. The use of only one media enables avoiding liquid junction potentials. The tip 7 of the patch clamp electrode 8 holding the patch-clamped cell 9 is preferably positioned approximately 5–25 μm from the capillary outlet 4 by means of at least one micropositioner 10, 11 controlling the capillary and/or the path clamp electrode. According to one embodiment, the whole system is placed in a Faraday cage (not shown). The patch clamp electrode is connected to a I-V-converter 12. In order to facilitate positioning of the capillary and the patch clamp electrode holding the cell, the cell bath is preferably placed on a microscope objective 13.

Figure 3A:
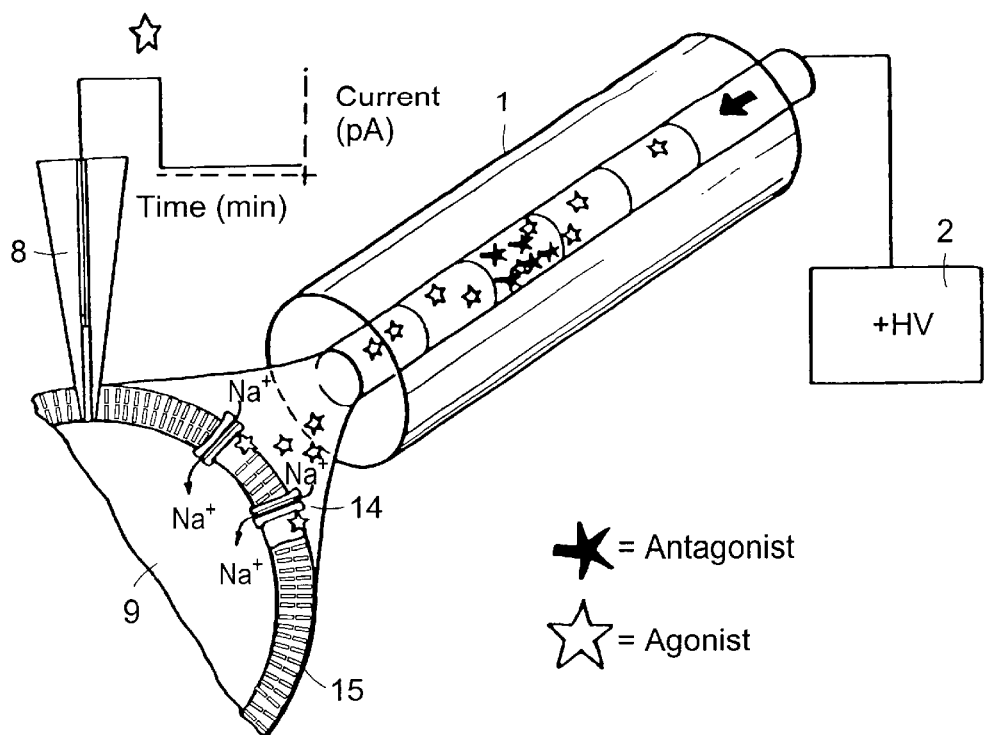
Figure 3B:
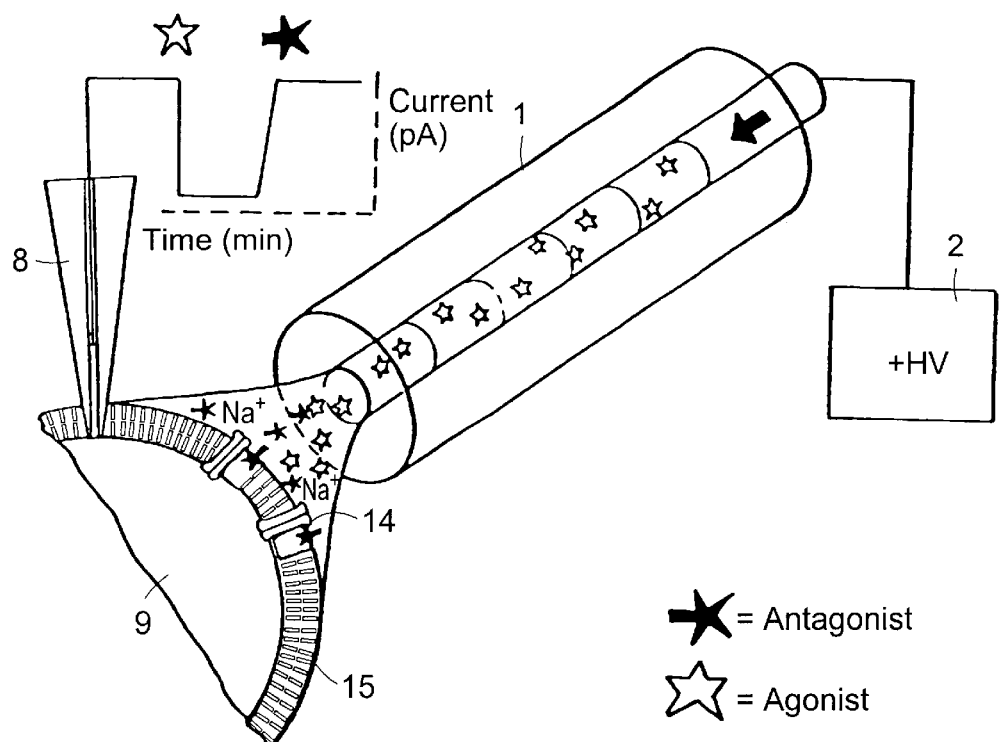

The function of the biosensor, in this case a patch-clamped cell, is illustrated in FIGS. 3A and 3B.

The capillary electrophoresis capillary 1 in FIG. 3A is filled with a receptor agonist-supplemented buffer with its flow directed onto the surface of a patch clamped cell 9. The receptor agonists, shown in FIGS. 3A and 3B as unfilled stars, continuously activate the ligand-gated ion channels 19 in the cell membrane 20 which, in this case, are permeable to sodium ions. Thus, when the receptor agonists bind to the receptors the sodium channels open and sodium ions diffuse from the outside of the cell into the cytoplasm. This flux of ions can be measured with the patch clamp electrode 8, preferably an Ag/AgCl-electrode, connected to a patch clamp amplifier, as an inward current, provided that the cell membrane is kept at a constant potential. In the capillary 1 there are also receptor antagonists, shown in FIGS. 3A and 3B as filled tailed stars, i.e. the compound that are to be screened, which have been injected into the capillary 1 and have migrated a distance proportional to the charge-to-friction drag ratio of the receptor antagonist and the applied field strength.

In FIG. 3B the receptor antagonists have migrated through the entire length of the capillary electrophoresis capillary 1 and started to antagonize the binding of receptor agonists. When the receptor antagonists bind to the receptors, the sodium permeable ion channel close and the inward transmembrane currents decrease. This decreased current is detected with the patch clamp electrode 8.

According to this preferred embodiment of the invention the receptors in the cell membrane are constantly activated by bathing of the cells in a solution containing specific receptor agonists. Preferably the separation technique used, in this case capillary electrophoresis, both deliver the receptor agonists and fractionates the receptor antagonists.

Thus, this preferred embodiment of the invention can be used for detection of any natural and synthetic receptor antagonists or receptor modulators that inhibit or negatively modulate receptor/ion-channel functions and effectively decrease receptor agonist-evoked membrane currents. This preferred embodiment of the invention thus offers possibilities to identify endogenous and synthetic receptor antagonists and to determine their mode of action on any ionotropic receptor system.

Another advantage of this preferred embodiment of the invention is that when ionotropic receptors are used in the capillary electrophoresis-patch clamp system, it is possible to gain full recovery of the detection system in milliseconds after the bioactive molecule has been washed away from the cell.

Another preferred embodiment of the present invention relates to re-activation of desensitising detector systems coupled to pulsed superfusion, i.e., superfusion of the desensitised biosensor is used to resensitise the biosensor. This can be performed by pulsing the activation of the biosensor by delivery of the receptor agonist to the biosensor for short period of times, said periods being separated by other periods when no agonist is delivered to the biosensor, which is further described below.

According to the present invention it is thus possible to improve the resolution of the detected bioactive analytes by using a method or apparatus according to which a pulsed flow of a buffer solution washes an area around the biosensor constituting the detector which is coupled to a separation system. Practically, this can be performed in two ways, as illustrated in FIGS. 4A–C, and FIG. 5, respectively.

The strategy illustrated in FIGS. 4A–C involves two capillaries. One of the capillaries, capillary 1, is used for electrophoretic separations and for delivery of the agonist to the biosensor, and the other capillary 14 is used for delivery of buffer, for rinsing of the biosensor, in front of the capillary outlet. A means 15 fixes the capillaries 1, 14 parallelly together. The position of the capillaries fixed together is controlled by a micromanipulator 10. In this system a switching mode places the patch-clamped cell 9 either at the outlet of the capillary 14 coupled to the superfusion system 16—position one— or at the outlet of the electrophoresis capillary 1—position two, as illustrated in FIGS. 4B and 4C. In FIG. 4B the situation when the cell is placed in position one is illustrated. In this position the receptors at the cell-surface are resensitised due to superfusion of the cell by a physiological compatible buffer when the cell is position one. In FIG. 4C the situation when the cell is placed in position two is illustrated. In this position the electrophoretically separated analytes are detected by means of patch-clamp. Thus by shifting the capillaries at a specific frequency a train of desensitised responses is attained, an example of which is illustrated in FIG. 1C.

Figure 5A:
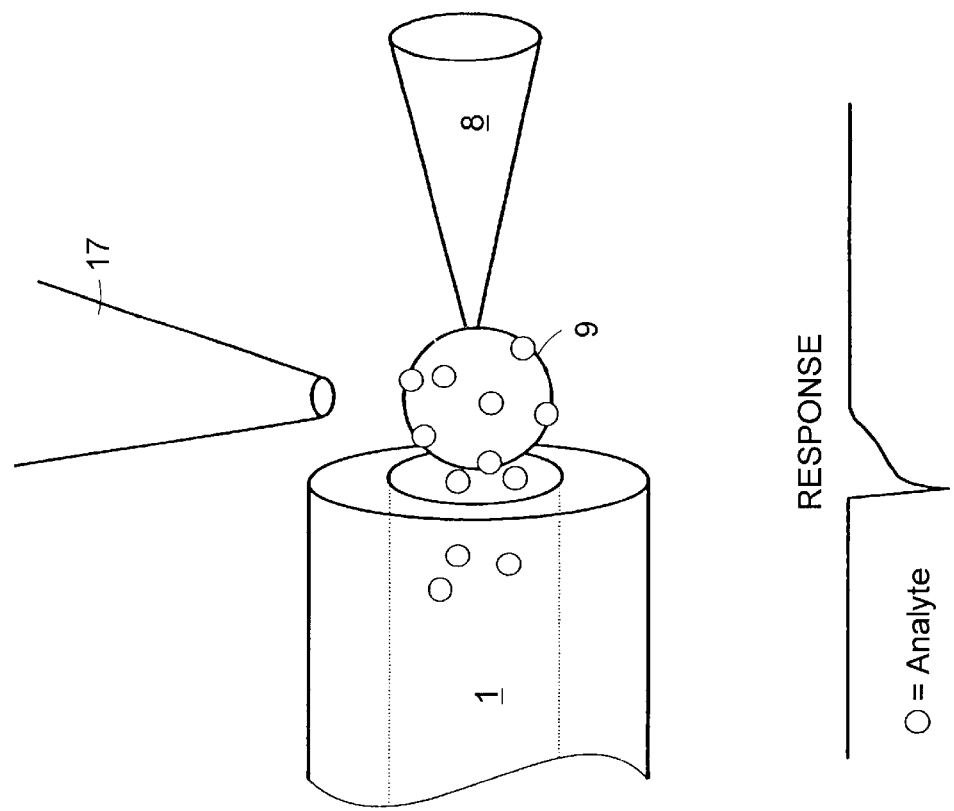
Figure 5B:
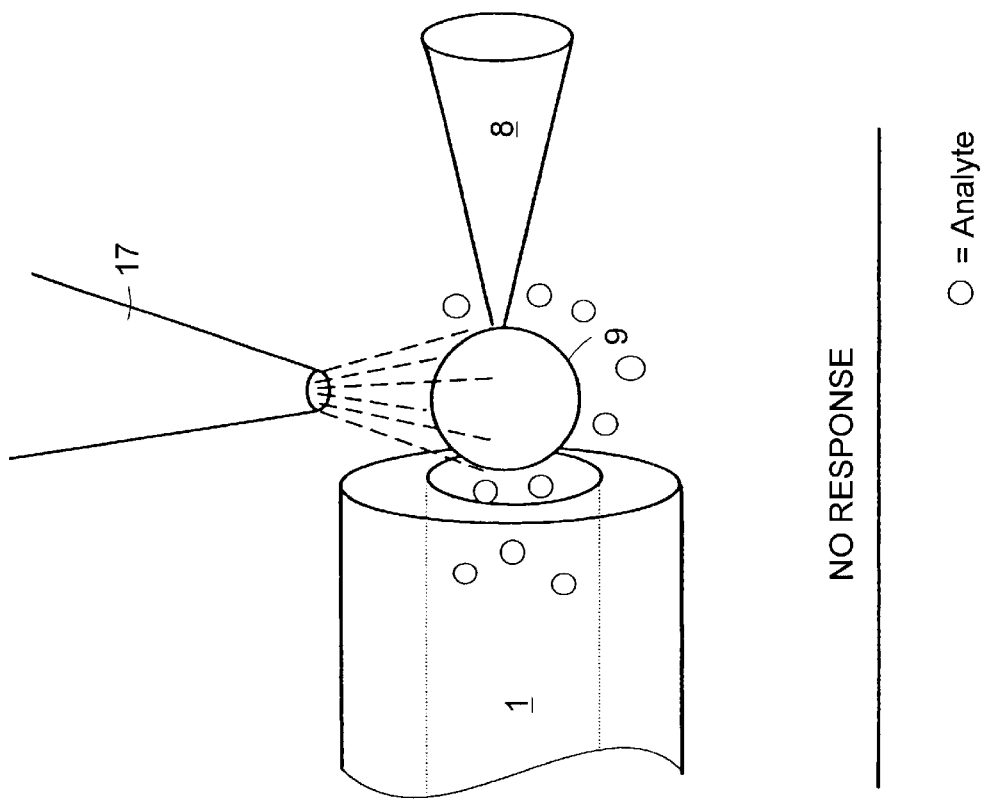

A second strategy is illustrated in FIGS. 5 A and 5 B. This set up involves a superfusion system comprising a glass micropipette 17 which is placed close to the cell 9 in the vicinity of the capillary outlet 4. The buffer flow applied from the glass-micropipette 17 leads to washing of the analytes from the surface of the patch clamped cell 9, as shown in FIG. 5 A. The dissociation of the analytes from the receptors makes the cell detector resensitised. When the buffer flow is interrupted, as shown in FIG. 5B, the electrophoretically separated analytes are able to bind to the receptors at the cell surface and an ion-channel mediated current is recorded by the patch-clamp amplifier system. The buffer flow from the pipette 17 is pulsed at a specific frequency by a external device (not shown in the Figure) thereby reactivating the receptors for detection. The pulsing device can be any appropriate device known to persons skilled in the art (see e.g. Smart, T. G., J. Physiol. 447:587, 1992).

EXAMPLES

These examples are intended to further illustrate the invention and should in no way be considered to limit the scope of the invention.

In the examples below the following materials and methods were used.

Biosensor-compatible Buffers

Separation of mixtures of glutamate receptor antagonists were performed using cell-based biosensor-compatible buffers. A cell-based biosensor-compatible buffer is a buffer which effectively keeps the cell-based biosensor in a functional and viable condition during the course of the experiment or the analysis procedure. slightly modified standard HEPES-saline buffer containing 140 mM NaCl, 5 mM KCl, 1 mM $MgCl_2$, 1 mM $CaCl_2$, 10 mM glucose and 10 mM HEPES (pH 7.4, NaOH) was used as extracellular and capillary buffer in examples 1 and 2 except in the separation of $Mg^{2+}$ where $MgCl_2$ were omitted. As described in the examples, the preferred agonist were only—included in the capillary solution.

Acute Isolation of Neurons from the Olfactory Bulb of the Rat

The cells used were interneurons from rat olfactory bulb acutely isolated according to the procedures described by Jacobson et al. (see Jacobson, I., Neurosci. Res. Comm. 8:11, 1991, and Jacobson, I., et al., Neurosci. Res. Comm. 10:177, 1992).

Newborn or adult rats (10–200 g) were anaesthetized with halothane (ISC Chemicals Ltd., Avonmouth, England) and decapitated. The olfactory bulbs were dissected and sliced into four pieces and placed in an incubation chamber. The chamber contained proteases from *Aspergillus oryzae* (2.5 mg/ml) which were dissolved in pre-warmed (32° C.) HEPES-saline buffer (see above). After 25–30 min., the slices were washed with the same buffer solution for 20 min. The solutions were constantly perfused with 95% $O_2$ and 5% $CO_2$ during both the enzymatic treatment arid the washing. The slices were then kept at 20° C. in a HEPES-saline buffer containing 1 mM $CaCl_2$, and bubbled with 950 $O_2$ and 5% $CO_2$. The slices were then disintegrated by shear forces by gentle suction through the tip of a fire-polished Pasteur pipette. The cell suspension was then placed in a Petri dish and diluted with a $Ca^{2+}$—containing (1 mM) HEPES-saline buffer. The Petri dish was transferred to the microscope stage. Viable interneurons were harvested up to six hours after the interruption of the enzymatic treatment. Chemicals and enzymes were obtained from Sigma (St Louis, Mo., USA).

Capillary Electrophoresis

The capillary electrophoresis separations were performed in fused silica capillaries (length: 25–50 cm, inner diameter: 50 $\mu$m) from Polymicro Tech., Phoenix, Ariz. USA. The electrophoresis was performed by applying a positive potential of 12 kV to the inlet of the capillary by a high voltage supply, manufactured by LKB, Bromma, Sweden. Since the high voltages produce electrical field strengths of several hundred volts per centimeter, the outlet of the capillary was fractured and grounded 5 cm above the outlet to create an almost field free region at the position of the cell detector. The injections were made hydrodynamically by placing the capillary inlet in sample solution 20 cm above the outlet end for 10 sec.

Patch-clamp Detection

The patch clamp detection was performed in the whole-cell configuration as described by Hamill, et al. (see Hamill, O. P., et al, Pflug. Arch. 391:85, 1981). The tip of the patch clamp electrode was placed 5–25 $\mu$m from the center of the capillary outlet. Patch pipettes were fabricated from thick-walled borosilicate glass (code no GC150-10, Clark Electromedical Instruments, Pangboume, Reading, UK). The diameters and the resistances of the tips were about 2–5 $\mu$m and 5–15 M$\Omega$, respectively. The estimated series resistance was always less than 50 M$\Omega$. The experiments were performed at room temperature of 18–22° C. The electrodes (reference and patch electrodes), contained a solution of 100 mM KF, 2 mM $MgCl_2$, 1 mM $CaCl_2$, 11 mM EGTA, 10 mM HEPES; the pH was adjusted to 7.2 with KOH.

The signals were recorded with a patch clamp amplifier (Model List L/M EPC-7, List-Electronic, Darmstadt, Germany), digitized (20 kHz, PCM 2 A/D VCR adapter, Medical Systems Corp., NY, USA), and stored on videotape. For the production of electropherograms the signals from the videotape were digitized at 2 Hz.

It is of outmost importance to sample the signals at proper rates for gaining complete information.

For spectral analysis of whole-cell currents (see Colquhoun, D., et al., Proc. R. Soc. Lond. B. Biol. Sci. 199:231, 1981) the signal from the videoadaptor was filtered with an 8 pole Butterworth filter (bandwith 3 kHz) and digitized at 6 Hz. Records were divided into 0.7 s blocks prior to calculation of the spectral density and the mean power spectrum was calculated by averaging all power spectra obtained from these blocks (at least 20). The receptor agonist-induced power spectra were subtracted from power spectra obtained during membrane resting conditions. The resulting power spectra were fitted by a double Lorentzian function using a least-squares Levenberg-Marquardt algorithm with proportional weighting.

The relationships between the current and the voltage (I-V) were obtained from current responses evoked by continuous perfusion of receptor agonist, and from blocked responses activated by electrophoretically separated receptor antagonist. The holding potential was changed by using a voltage ramp (−80 to +40 mV, duration 3 to 7 s, pClamp software, Axon Instruments; Foster City, Calif., USA). For elimination of responses evoked by voltage-dependent ion channels, the I-V curve obtained between the responses were subtracted from the ramp obtained during the receptor agonist- or receptor antagonist-activated responses.

Example 1

Separation and Detection of $Mg^{2+}$

In this example $Mg^{2+}$ ions, that reversibly block the N-methyl-D-aspartate receptor in a voltage-dependent manner, were separated and detected by the patch-clamped cells.

The N-methyl-D-aspartate receptors on the cells were activated by N-methyl-D-aspartate (agonist) and glycine (co-agonist), continuously delivered from the electrophoresis capillary.

The electrolyte in the capillary electrophoresis capillary and in the inlet vial used in this example was a $Mg^{2+}$—free HEPES-saline containing 200 µM N-methyl-D-aspartate (NMDA) and 20 µM glycine. The same buffer was used in the cell bath, but without NMDA and glycine.

Figure 6A:
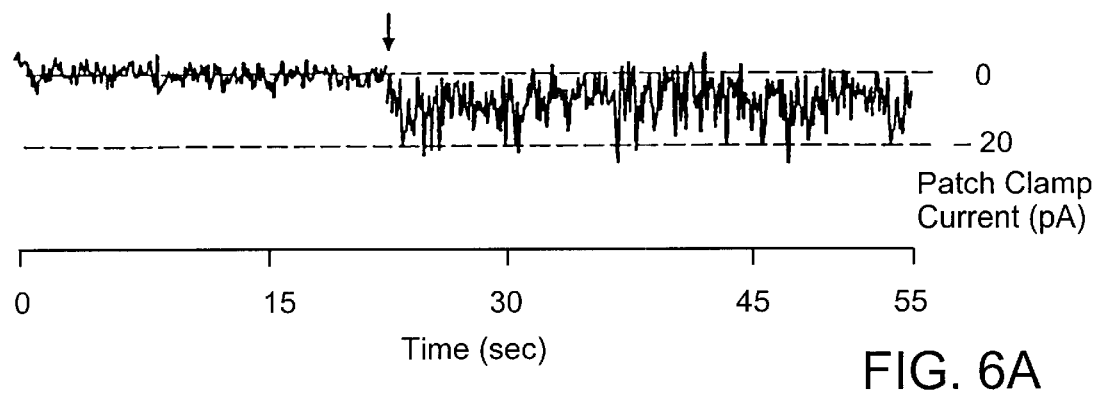
Figure 6B:
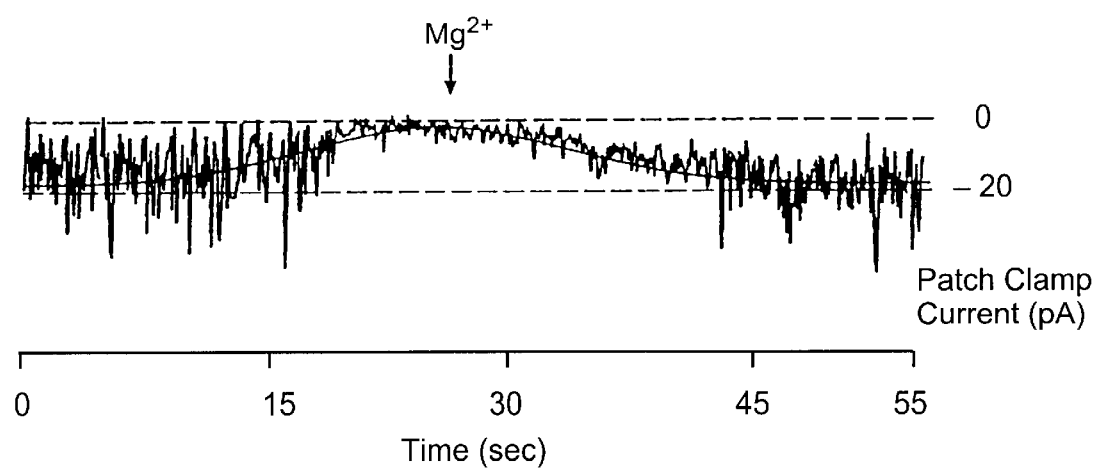

In FIG. 6 A there is a control trace showing activation of NMDA receptors by NMDA (200 µM) and glycine (20 µM), delivered to the cell through the capillary electrophoresis capillary. The response occurs immediately following the start of the electrophoresis.

$Mg^{2+}$ ions (2 mM) hydrodynamically injected into the electrophoresis capillary migrate through the capillary in less than a minute and are detected as a transient Gaussian-distributed attenuation of N-methyl-D-aspartate-activated current responses at a holding potential of −70 mV.

This is illustrated in FIG. 6 B by an electropherogram showing a blocked response of the NMDA receptor mediated current by separated $Mg^{2+}$ ions migrating at approximately 20 s. The response is fitted to a Gaussian function.

Figure 6C:
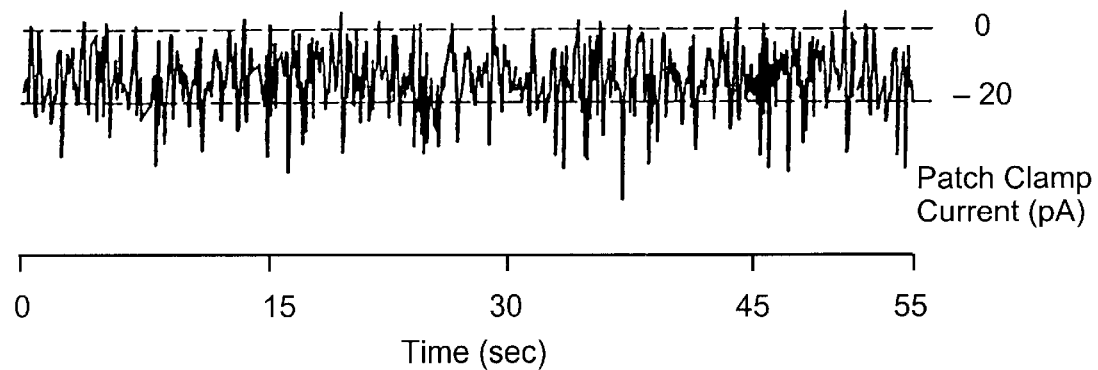

In FIG. 6C there is a control trace presenting the unaffected NMDA receptor response after injection of HEPES-saline containing 200 µM NMDA and 20 µM glycine.

Figure 7:
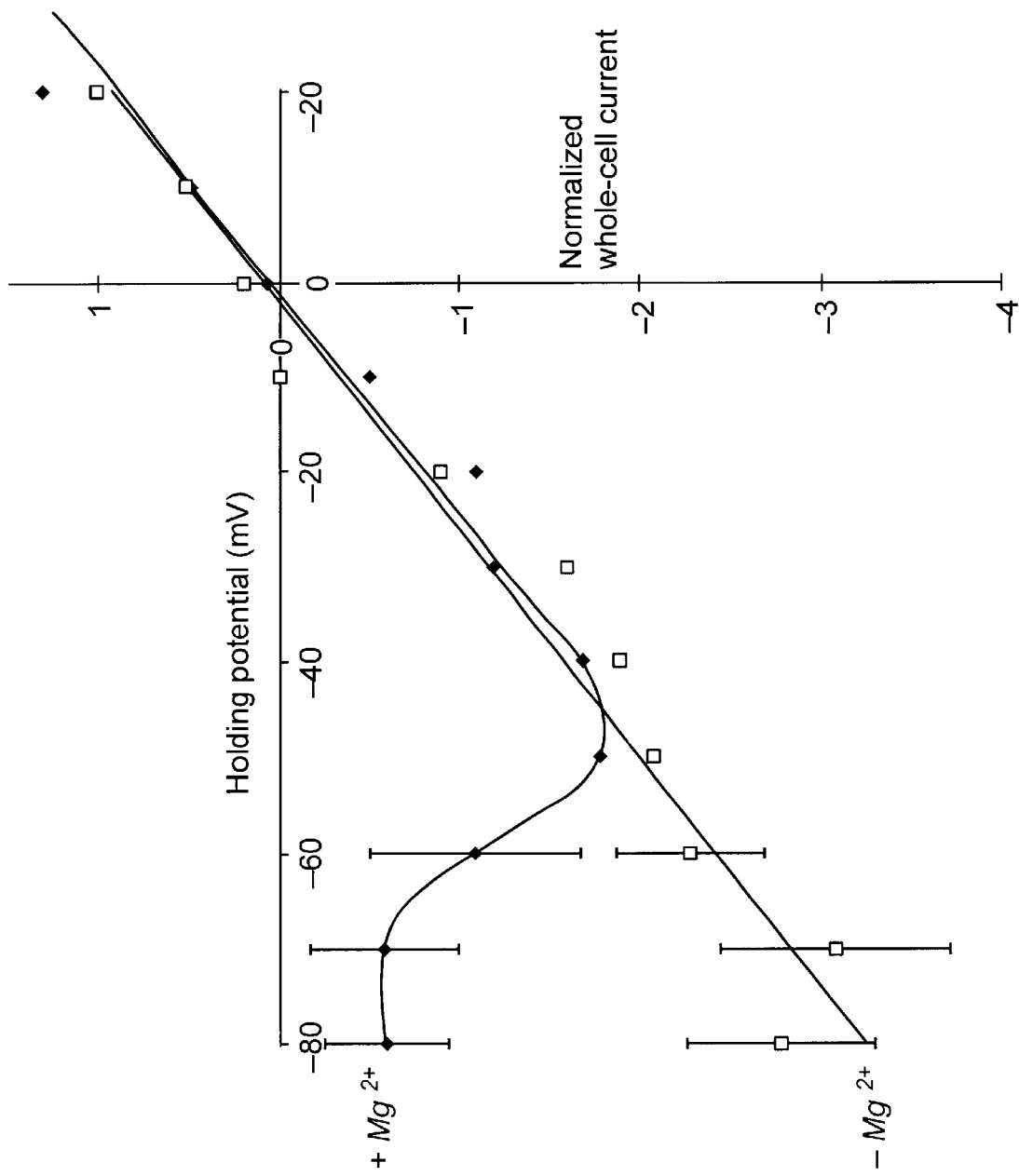
FIG. 7 shows current-to-voltage relationships obtained during constant activation of the NMDA receptor and during the attenuation of this response by separated $Mg^{2+}$ ions.

The current-to-voltage relationships obtained during constant activation of the NMDA receptor and during the attenuation of this response by separated $Mg^{2+}$ ions are shown in FIG. 5. The relationships display the characteristic features, i.e. blockade of inward currents at membrane resting potentials and unaltered outward currents at positive potentials. The current-to-voltage relationship for the NMDA receptor by activation of NMDA in $Mg^{2+}$-free media is represented by open squares, and in $Mg^{2+}$-containing media by filled diamonds. The plot in FIG. 7 is based on averages of three normalized current amplitudes at each decade (from −80 mV to +40 mV).

Example 2
Separation and Detection of 6-Cyano-7-Nitroquinoxaline-2,3-Dione and 6,7-Dichloro-3-Hydroxy-2-Quinoxaline-Carboxylic Acid Since glutamate receptors are implicated in a wide range of diseases in the central nervous system (CNS) of mammals, including Alzheimer's disease and Parkinson's disease, and CNS dysfunctional processes such as epilepsy and neuronal death due to mechanical trauma and stroke, 6-cyano-7-nitroquinoxaline-2,3-dione and its analogues can be useful as drugs protecting against such diseases and disorders (see Honore, T., et al., Science 241: 701(1988).

6-cyano-7-nitroquinoxaline-2,3-dione (CNQX) and 6,7-dichloro-3-hydroxy-2-quinoxaline-carboxylic acid (DCQXC), both which reversibly block α-amino-3-hydroxy-5-methyl-4-isoxazolepropionate (AMPA) and kainate (KA) receptors, belonging to the glutamate receptor superfamily, were separated by capillary electrophoresis and detected online by patch-clamped cells.

The electrolyte in the capillary electrophoresis capillary, the medium in the cell bath and the buffer used in this example are the same as used in example 1, with the exception that the agonist in this example was kainate instead of NMDA and glycine.

Non-desensitising AMPA receptors were activated by 100 µM KA (agonist) continuously delivered from the electrophoresis capillary.

Figure 8:
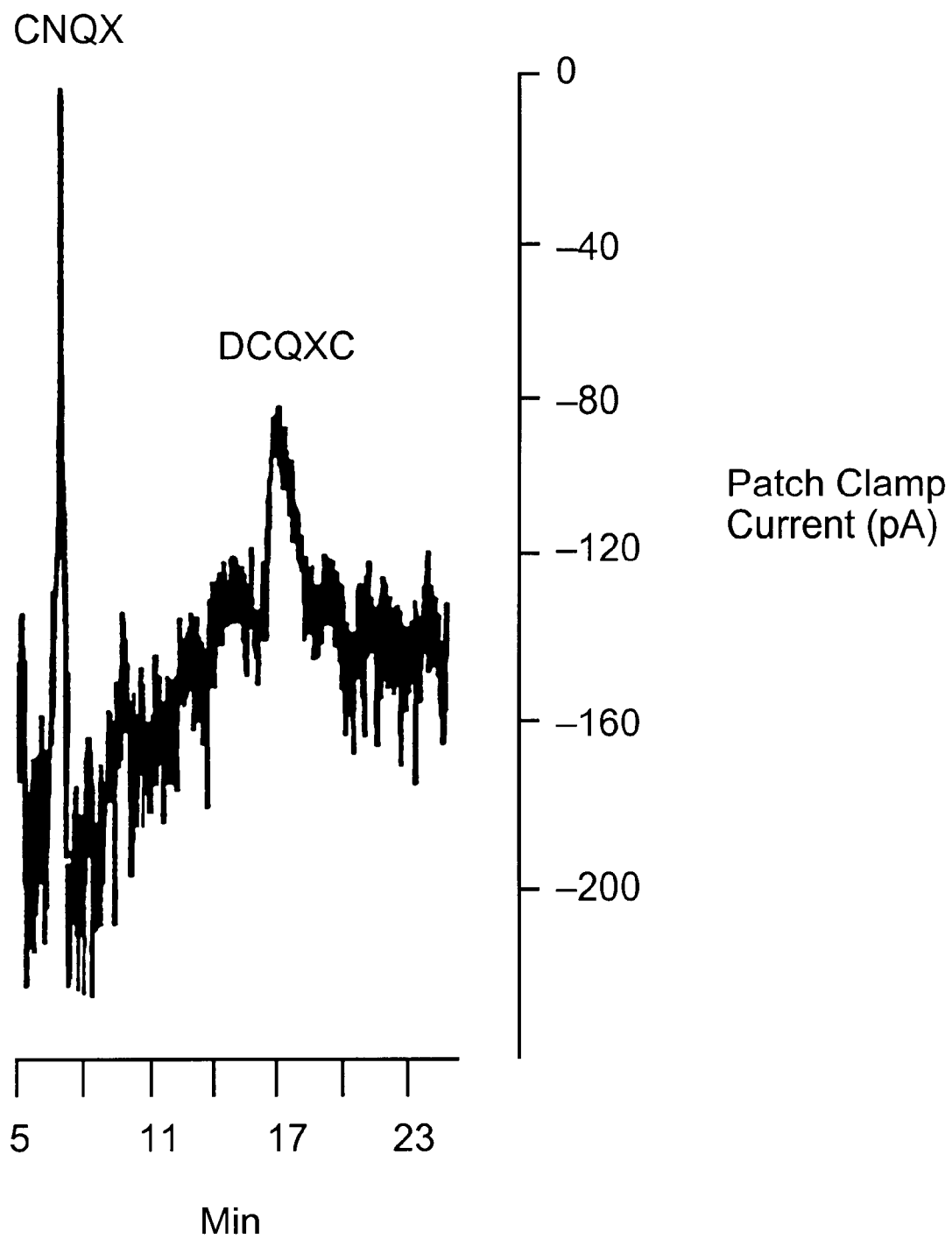
FIG. 8 shows an electropherogram illustrating patch clamp detection in capillary electrophoresis of 6-cyano7-nitroquinoxaline-2,3-dione (CNQX) and 6,7-dichloro-3-hydroxy-2-quinoxaline-carboxylic acid (DCQXC).

At a holding potential of −70 mV CNQX and DCQXC were detected at characteristic migration times as transient attenuations of KA-activated current responses. This is shown in FIG. 8.

What is claimed is:

1. An apparatus for detecting a modulator of a receptor or ion channel, comprising:
   (a) a patch-clamped biosensor;
   (b) a first capillary electrophoresis separation capillary for fractionating a sample comprising the modulator;
   wherein the separation capillary comprises:
      (i) a sample inlet part which is connected to a high-voltage power supply through a buffer vial containing a buffer supplemented with a receptor agonist; and
      (ii) a grounded outlet which ends close to the patch-clamped biosensor that is activated by the receptor agonist and deactivated by fractional antagonist, wherein the outlet delivers a fraction comprising the modulator to the biosensor;
   (c) a patch clamp electrode in electrical communication with the patch-clamped biosensor and a recording apparatus for recording currents detected by the patch clamp electrode;
   (d) a second capillary having an outlet for delivery of a buffer not comprising any agonist to the biosensor, said second capillary having an inlet connected to a superfusion system; and
   (e) means for switching a position of the first and second capillaries so that the patch-clamped biosensor alternatively is placed in front of the outlet of the first capillary and in front of the outlet of the second capillary.

* * * * *